United States Patent [19]

Shu et al.

[11] 4,200,741

[45] Apr. 29, 1980

[54] USE OF CRYSTALLINE PURE OR SUBSTANTIALLY PURE 2,4,6-TRI-ISOBUTYL-1,3,5-DITHIAZINE AND PROCESS FOR PREPARING SAME

[75] Inventors: Chi-Kuen Shu, Cliffwood; Braja D. Mookherjee, Holmdel; Manfred H. Vock, Locust, all of N.J.

[73] Assignee: International Flavors & Fragrances Inc., New York, N.Y.

[21] Appl. No.: 961,684

[22] Filed: Nov. 17, 1978

[51] Int. Cl.$^2$ ............................................. C07D 285/00
[52] U.S. Cl. ................................................... 544/5
[58] Field of Search ...................................... 544/5

[56] References Cited

U.S. PATENT DOCUMENTS

| 2,273,664 | 2/1942 | Searle | 544/5 |
| 2,610,182 | 9/1952 | McDermott | 544/5 |
| 3,650,771 | 3/1972 | Wiener | 99/140 |

FOREIGN PATENT DOCUMENTS 953519  3/1964  United Kingdom ........................ 544/5

Primary Examiner—John M. Ford
Attorney, Agent, or Firm—Arthur L. Liberman; Franklin D. Wolffe

[57] ABSTRACT

A small but effective amount of a pure crystalline or substantially pure compound represented by the formula:

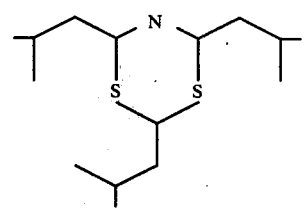

is used to alter, modify or enhance the flavor and aroma characteristics of a foodstuff having a bacon flavor and aroma.

2 Claims, 4 Drawing Figures

GLC PROFILE
EXAMPLE I

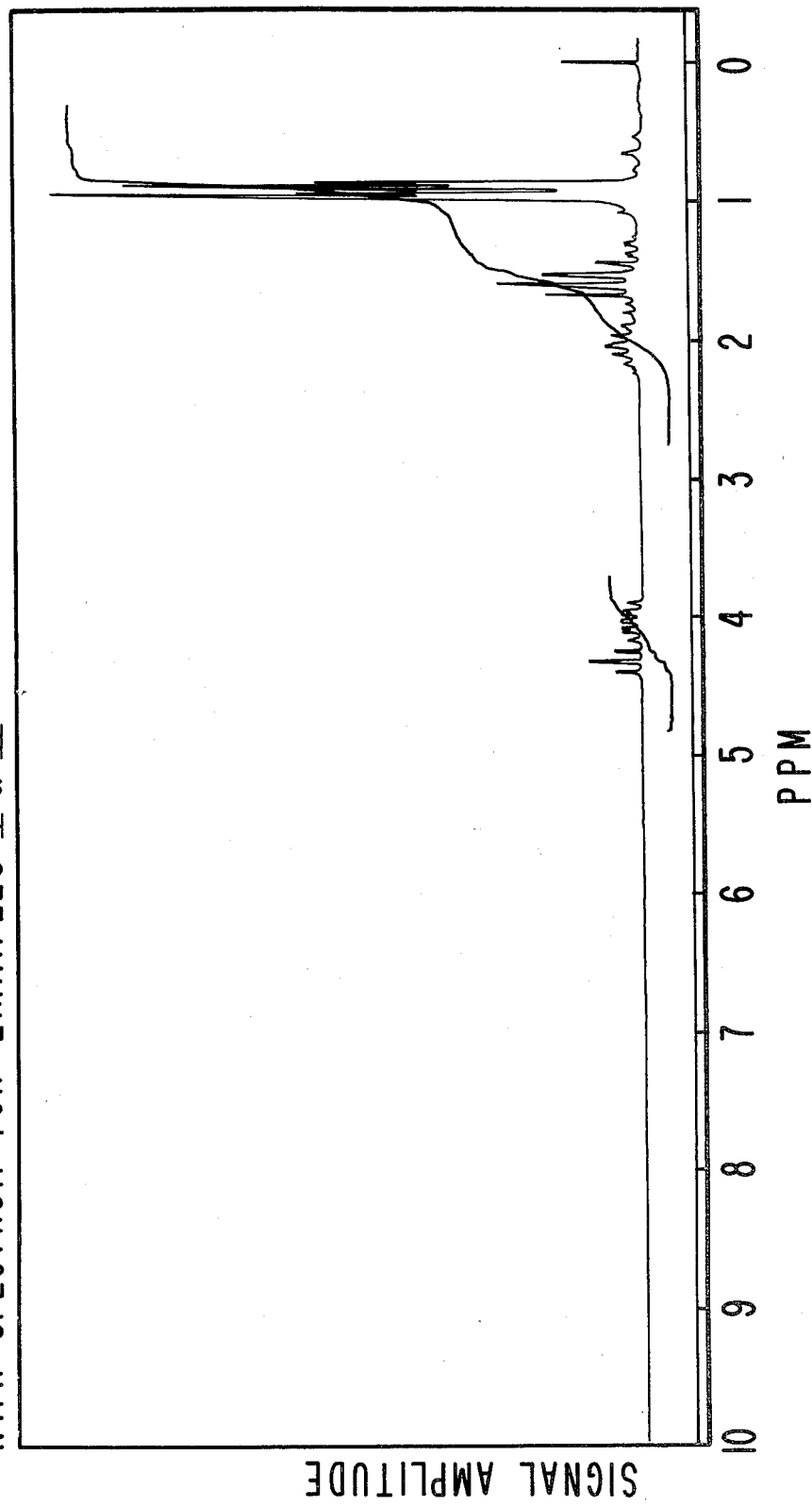

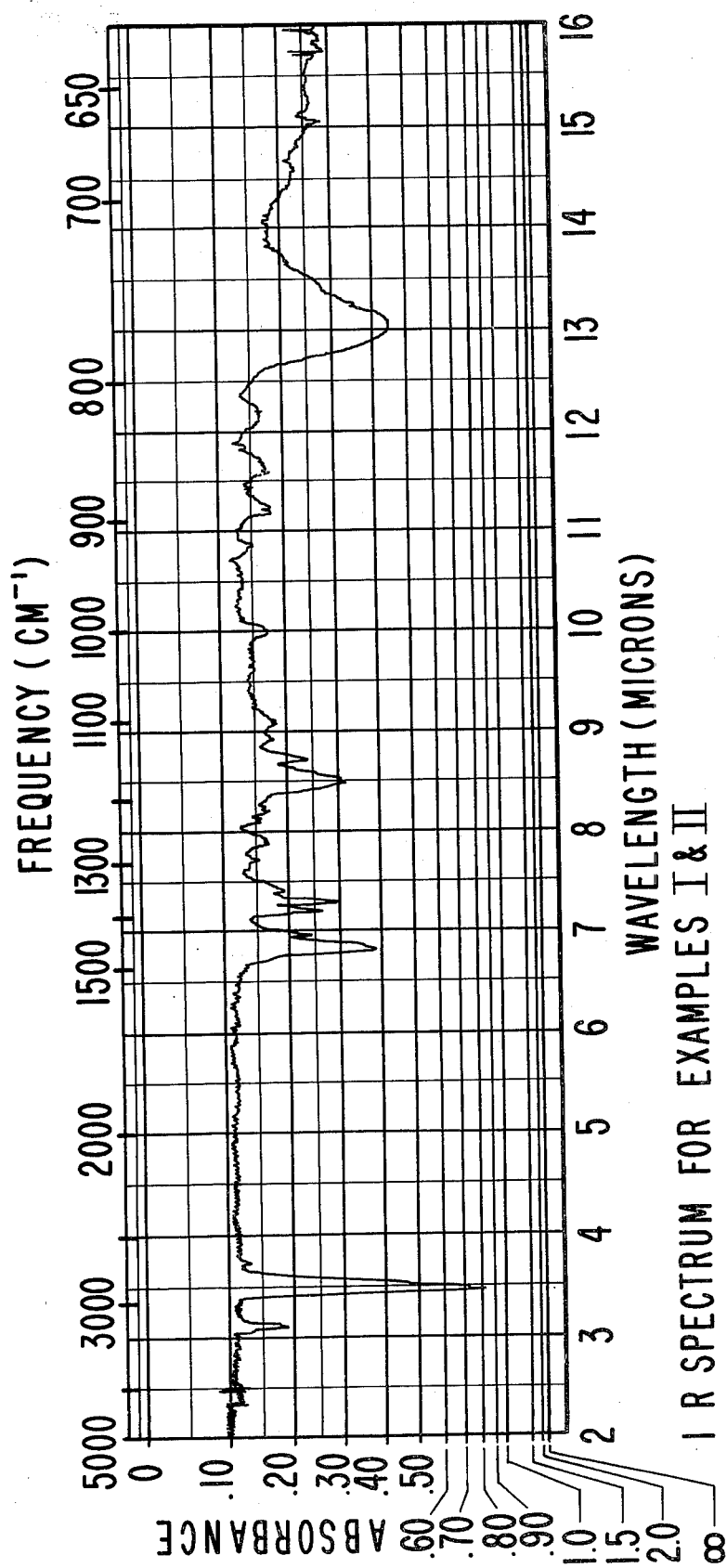

USE OF CRYSTALLINE PURE OR SUBSTANTIALLY PURE 2,4,6-TRI-ISOBUTYL-1,3,5-DITHIAZINE AND PROCESS FOR PREPARING SAME

BACKGROUND OF THE INVENTION

This invention pertains to the use of a certain dithiazine to alter, modify or enhance the flavor and aroma of a foodstuff having a bacon flavor and aroma.

There is a continuing search for compositions which can vary, fortify, modify, enhance or otherwise improve (i.e. alter) the flavor and aroma of a foodstuff. To be fully satisfactory, such compositions should be stable, non-toxic and blendable with other ingredients to provide their own unique flavor and aroma nuance without detracting from the co-ingredients. Preferably, such compositions should be naturally occurring or present in natural foodstuffs (although unrecognized as flavor components thereof) so that their ingestible safety can be readily recognized. Additionally, these materials should be capable of being synthesized in a simple and economic manner.

Ingredients for foodstuff flavors having aromas and tastes which are compatible from an esthetic standpoint and from a chemical standpoint with meats and meat flavors are particularly desirable. More specifically, roasted, fried and fried bacon aroma characteristics and flavor characteristics are particularly useful for bacon flavors and, in addition, they useful for roasted meat, roasted nut and fowl (e.g. chicken and duck) foodstuff flavors and to augment and enhance such flavors.

U.S. Pat. No. 3,966,988 discloses the use of a small but effective amount of a compound represented by the formula:

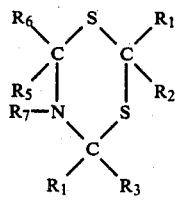

wherein $R_1$, $R_3$, and $R_5$ are the same and are lower alkyl of from 1 to 5 carbon atoms, $R_2$, $R_4$, and $R_6$ are hydrogen, and $R_7$ is hydrogen or lower alkyl of from 1 to 5 carbon atoms; is used to alter, modify or enhance the flavor and aroma characteristics of foodstuffs, perfumes and perfumed articles. Specifically disclosed and exemplified is the compound 2,4,6-trimethyldihydro-1,3,5-dithiazine. This compound is also specifically characterized. In addition, however, the compound 2,4,6-tri-isobutyldihydro-1,3,5-dithiazine is disclosed but is not specifically characterized in said U.S. Pat. No. 3,966,988. Nor is the pure crystalline form of said 2,4,6-tri-isobutyldihydro-1,3,5-dithiazine disclosed therein.

Bacon flavor itself is prepared according to U.S. Pat. No. 3,650,771 issued on Mar. 21, 1972. In said U.S. Pat. No. 3,650,771 the reaction product of 2-aminoethanol hydrosulfide and isovaleraldehyde is indicated to give a strong crisp bacon product when said 2-aminoethanol hydrosulfide and isovaleraldehyde are mixed together and heated over a temperature of 70°–80° C. for a period of about five minutes. It is noteworthy that the bacon flavor and aroma of the compound having the structure:

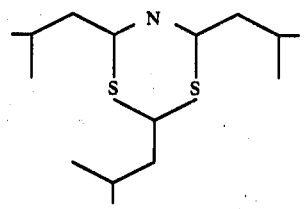

is surprisingly intense and longer lasting than is the bacon flavor and aroma of any of the reaction products of U.S. Pat. No. 3,650,771, particularly the reaction products of 3,650,771, particularly the reaction product of 2-aminoethanol hydrosulfide and isovaleraldehyde. On the other hand, the compound having the structure:

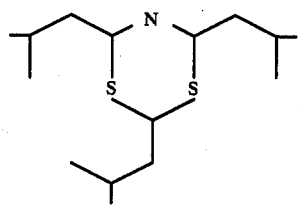

can be extracted by means of high pressure liquid chromatography from the reaction mixture resulting from the reaction of 2-aminoethanol hydrosulfide with isovaleraldehyde at a temperature of 70°–80° C. for five minutes and at other temperatures and times also.

Compound having the structure:

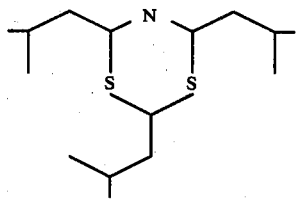

is specifically disclosed by Beilstein at Vol. 1-V-27 (4) wherein it is indicated to have the common name "Valeraldin" and can be synthesized by reacting ammonia with thioisovaleraldehyde.

No mention is made in any of the prior art including the Beilstein reference and U.S. Pat. No. 3,966,988 issued on June 29, 1976 of the existence of pure crystalline or substantially pure 2,4,6-tri-isobutyl-1,3,5-dithiazine or the use thereof as a bacon flavor ingredient for enhancement, imparting or augmenting properties.

BRIEF DESCRIPTION OF THE DRAWINGS

FIG. 3 is the NMR spectrum for fractions 17 and 18 resulting from the high pressure liquid chromatographic separation of the reaction product of Example I. It is pure crystalline or substantially pure 2,4,6-tri-isobutyl-1,3,5-dithiazine.

FIG. 4 is the infrared spectrum for fractions 17 and 18 of the high pressure liquid chromatographic separation product of Example I, crystalline 2,4,6-tri-isobutyl-1,3,5-dithiazine.

THE INVENTION

Figure 1:
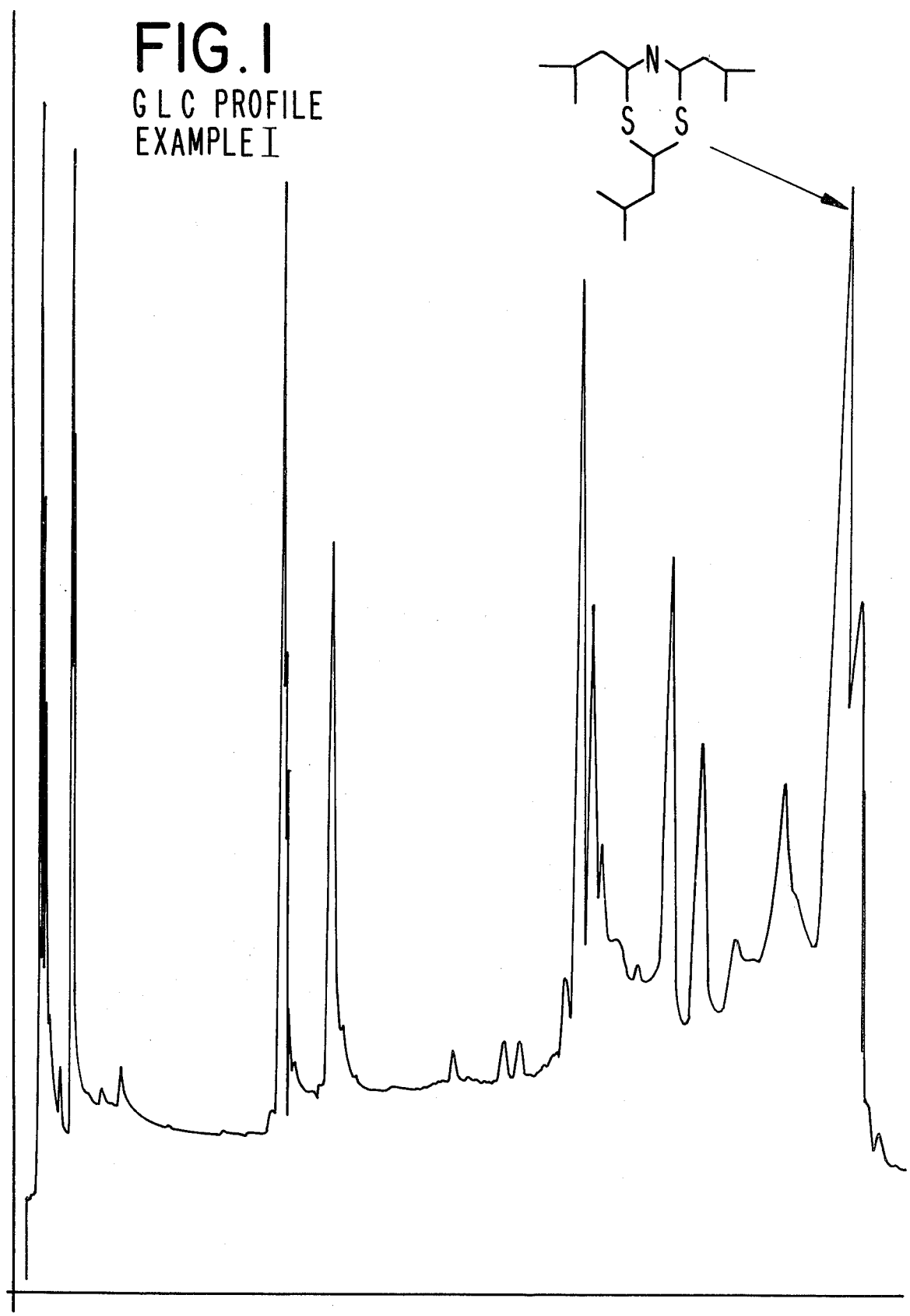
FIG. 1 is the GLC profile of the reaction product produced according to Example I wherein isovaleraldehyde and ammonia is reacted in the presence of hydrogen sulfide.

This invention has to do with the use of pure crystalline or substantially pure 2,4,6-tri-isobutyl-1,3,5-dithiazine to alter, modify, enhance the flavor and aroma of a foodstuff having a bacon flavor or impart a bacon flavor to a foodstuff.

The pure crystalline or substantially pure 2,4,6-tri-isobutyl-1,3,5-dithiazine of our invention has a structure:

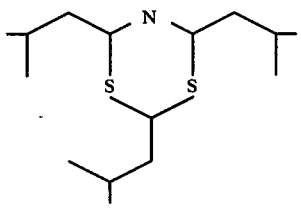

and has roasted, fried and fried bacon aroma and flavor characteristics and in addition a roasted potato skin flavor characteristic causing it to be useful in roasted meat, roasted nut, bacon and fowl flavors. A physical form of 2,4,6-tri-isobutyl-1,3,5-dithiazine, being in pure and crystalline or substantially pure form is novel per se. The process for preparing same is also novel in that heretofore high pressure liquid chromatographic techniques have never been used to obtain such a compound from a reaction product.

The 2,4,6-tri-isobutyl-1,3,5-dithiazine of our invention in pure crystalline or substantially pure form is obtained by first reacting isovaleraldehyde with ammonia to form a Shiff Base and reacting the resulting Shiff Base with hydrogen sulfide. The reaction of the isovaleraldehyde with ammonia takes place at a temperature of between 15° C. and 0° C. It is preferred that the mole ratio of ammonia: isovaler aldehyde is between 2:1 and 1:0.5 with a preferred mole ratio of 1:1.5. The resulting Shiff Base is then reacted with hydrogen sulfide at atmospheric pressure, preferably at room temperature over a period of time of between 1 and 5 hours, preferably 2-3 hours. Higher pressures may be used without detrimentally affecting the yield but no particular advantages obtained in using pressures above one atmosphere.

The reaction product is then extracted with an inert organic solvent such as anhydrous diethyl ether, the extract is then dried over such materials as anhydrous sodium sulfate and the solvent is stripped off by such means as a rotary evaporator. The resulting crude material is then microdistilled in order to get rid of low boiling fractions and the residue is subjected to column chromatography using such eluting materials as isopentane and/or thiethyl ether and isopentane in various percentages of diethyl ether and isopentane such as 0.5% and 1%. The resulting fractions from the first column chromatographic separation are subjected to column chromatography a second time using for example a silica column using as eluting agents isopentane, 0.5% diethyl ether in isopentane, 1% diethyl ether in isopentane and 2% diethyl ether in isopentane. A product resulting from the second column chromatography (combined fractions) are then subjected to high pressure liquid chromatography at a rate of between 100 and 500 ml per minute, preferably at about 350 ml per minute. The fractions are analyzed and selected for the purity of 2,4,6-tri-isobutyl-1,3,5-dithiazine in said fractions. In one such Example, fractions 17 and 18 were selected yielding 100% 2,4,6-tri-isobutyl-1,3,5-dithiazine in crystalline form after solvent evaporation.

The structural formula for 2,4,6-tri-isobutyl-1,3,5-dithiazine given herein contemplated and includes cis and trans and other conformational isomers. When the 2,4,6-tri-isobutyl-1,3,5-dithiazine in pure and crystalline or substantially pure form according to this invention is used in a flavoring composition, it can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners and flavor intensifiers.

The term "foodstuff" as used herein includes both solid and liquid ingestible materials for man or animals which materials usually do, but need not, have nutritional value. Thus, foodstuffs include meats, gravies, soups, convenience foods, malt and other alcoholic or non-alcoholic beverages, nut butters such as peanut butter and other spreads, seafoods including fish, crustaceans, mollusks and the like, candies, breakfast foods, baked goods, vegetables, cereals, soft drinks, snack foods, pet foods such as dog and cat foods, other veterinary products, and the like.

The terms "alter" and "modify" (in their application to foodstuffs) in its various forms will be understood herein to mean the supplying or imparting of a flavor character or note to an otherwise bland, relatively tasteless substance, or sugmenting and existing flavor characteristics where the natural flavor is deficient in some regard, or supplementing the existing flavor impression to modify the organoleptic character.

The term "enhance" is used herein to mean the intensification of a flavor or aroma characteristic or note without the modification of the quality thereof. Thus, "enhancement" of a flavor or aroma means that the enhancement agent does not add any additional flavor note.

Conventional flavoring materials as indicated above include saturated and unsaturated fatty and amino acids, alcohols, including primary and secondary alcohols; esters, carbonyl compounds including ketones and aldehydes; lactones, other cyclic organic materials including benzene derivatives, alicyclics, heterocyclics such as furans, pyridines, pyrazines and the like; sulfur-containing materials including thiols, sulfides, disulfides and the like; proteins; lipids; carbohydrates; so-called flavor potentiators such as monosodium glutamate, guanylates, and inosinates; natural flavoring materials such as cocoa, vanilla and caramel; essential oils and extracts such as anise oil, clove oil and the like; artificial flavoring materials such as vanillin; and the like. Particularly useful flavoring agents and adjuncts are cyclopentane thiol, protein hydrolysate, such as hydrolyzed vegetable protein, cysteine, salts of cysteine such as cysteine hydrochloride, thiamine, salts of thiamine, 2,5-dimethyl-3-hydroxy-4-oxo-4,5-dihydrofuran, and products resulting from heating a mixture of at least two differing materials of the foregoing and high pressure (2-10 atmospheres) reaction products of $H_2S$ and 2,5-dimethyl-3-hydroxy-4-oxo-4,5-dihydrofuran.

Stabilizers include preservatives such as sodium chloride, and the like; antioxidants such as calcium and sodium ascorbate, ascorbic acid, butylated hydroxyanisole, butylated hydroxytoluene, propyl gallate and the like; sequestrants such as citric acid, EDTA, phosphates, and the like.

Thickeners include carriers, binders, protective colloids, suspending agents, emulsifiers and the like, such as agar-agar, carrageenan, cellulose and cellulose derivatives such as carboxymethyl cellulose and methyl cellulose, natural and synthetic gums such as gum arabic, gum tragacanth and the like, and other proteinaceous material, lipids, carbohydrates, starches and pectins.

Surface active agents include emulsifying agents such as mono-and/or diglycerides of fatty acids such as caproic acid, caprylic acid, palmitic acid, myristic acid, oleic acid, and the like; lecithin; defoaming and flavor-dispersing agents such as sorbitan monostearate, potassium stearate, hydrogenated tallow alcohol, and the like.

Conditioners include compounds such as bleaching and maturing agents such as benzoyl peroxide, calcium peroxide, hydrogen peroxide and the like; starch modifiers such as peracetic acid, sodium chlorite, sodium hypochlorite; propylene oxide, succinic anhydride and the like; buffers and neutralizing agents such as sodium acetate, sodium diacid phosphate, ammonium bicarbonate, ammonium phosphate, citric acid, lactic acid, vinegar and the like; colorants such as carminic acid, cochineal, turmeric, curcumin, approved food and drug dyes, and the like; firming agents such as aluminum sodium sulfate, calcium chloride and calcium gluconate; texturizers; anti-caking agents such as aluminum calcium sulfate and tribasic calcium phosphate; enzymes, yeast foods such as calcium lactate and calcium sulfate; nutrient supplements such as iron salts, such as ferric phosphate, ferric pyrophosphate, ferrous gluconate and the like, riboflavin, vitamins; zinc sources such as zinc chloride, zinc sulfate, and the like.

The 2,4,6-tri-isobutyl-1,3,5-dithiazine in pure crystalline or substantially pure form, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The 2,4,6-tri-isobutyl-1,3,5-dithiazine in pure crystalline or substantially pure form can be incorporated with the carriers by conventional means such as spray-drying, drum drying, and the like. Such carriers can also include materials for coacervating the 2,4,6-tri-isobutyl-1,3,5-dithiazine in pure crystalline or substantially pure form (and other flavoring ingredients, as present) to provide encapsulated products. When the carrier is an emulsion, the flavoring composition can also contain emulsifiers such as mono- and diglycerides of fatty acids and the like. With these carriers of vehicles, the desired physical form of the composition can be prepared.

It will be understood by those skilled in the art that the 2,4,6-tri-isobutyl-1,3,5-dithiazine in pure crystalline or substantially pure form can be added to the materials to be flavored at any convenient point in the production of the finished product. Thus, when they are used to alter or otherwise vary the flavor of a foodstuff, they can be added in the original mixture, dough, emulsion, batter or the like, prior to any cooking or heating operation. Alternatively, they can be added at a later stage of processing if volatilization losses would be excessive during the earlier processing.

The quantity of 2,4,6-tri-isobutyl-1,3,5-dithiazine in pure crystalline or substantially pure form or mixtures thereof utilized should be sufficient to impart the desired flavor characteristic to the product, but on the other hand, the use of an excessive amount of the 2,4,6-tri-isobutyl-1,3,5-dithiazine in pure crystalline or substantially pure form is not only wasteful and uneconomical but in some instances too large a quantity may unbalance the flavor or other organoleptic property of the product to be consumed. The quantity used will vary depending upon the ultimate foodstuff or other consumable product; the amount and type of flavor initially present in the product; the further process or treatment steps to which the product will be subjected; regional and other preference factors; the types of storage, if any, to which the product will be subjected; and the preconsumption treatment, such as baking, frying, and so on, given to the product by the ultimate consumer.

It is accordingly preferred that the ultimate compositions contain from about 0.002 parts per million (ppm) to about 100 ppm of the 2,4,6-tri-isobutyl-1,3,5-dithiazine in pure crystalline or substantially pure form. More particularly, in food compositions it is desirable to use from about 0.02 to about 20 ppm and in certain preferred embodiments of the invention, from about 0.1 to about 15 ppm of the 2,4,6-tri-isobutyl-1,3,5-dithiazine in pure crystalline or substantially pure form are included in the finished product.

The amount of 2,4,6-tri-isobutyl-1,3,5-dithiazine in pure crystalline or substantially pure form to be utilized in flavoring or flavor-enhancing compositions can be varied over a wide range depending upon a particular quality to be added to the foodstuff, tobacco, or other consumable material. Thus, amounts of one or more 2,4,6-tri-isobutyl-1,3,5-dithiazine in pure crystalline or substantially pure form according to the present invention from about 0.02 up to 80 or 90% can be incorporated in such compositions. It is generally found to be desirable to include from about 0.02 to about 25% of the 2,4,6-tri-isobutyl-1,3,5-dithiazine in pure crystalline or substantially pure form in such compositions.

The following examples are given to illustrate embodiments of the invention as it is presently preferred to practice it. It will be understood that these examples are illustrative, and the invention is not to be considered as restricted thereto except as indicated in the appended claims.

All parts, proportions, percentages, and ratios herein are by weight unless otherwise indicated.

EXAMPLE I

PREPARATION OF PURE CRYSTALLINE OR SUBSTANTIALLY PURE 2,4,6-TRI-ISOBUTYL-1,3,5-DITHIAZINE

REACTION:

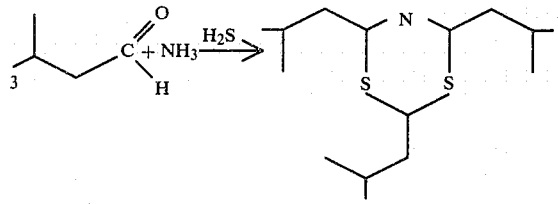

Into a 1 liter, 3-neck flask equipped with mechanical stirrer, addition funnel, thermometer and condenser is placed 350 grams of 30% aqueous ammonia with stirring at −9° C. 172 grams of isovaleraldehyde is added dropwise over a 45 minute period while maintaining the reaction temperature at between −10° C. and 0° C.

The addition funnel is then removed and the solids on the inside glass wall of the flask are washed with 150 ml water. The flask is then stoppered. The reaction mixture is then allowed to come to room temperature with stirring over a period of 130 minutes.

The flask is unstoppered and hydrogen sulfide gas is bubbled into the reaction mass over a period of 1 hour and 45 minutes via a gas dispersion tube.

Three hundred ml volumes of diethyl ether is then used to extract the organic layer. The ether extract is then washed with saturated sodium chloride-water until neutral and dried over anhydrous sodium sulfate. The solvent is then removed by means of a rotary evaporator and 150 grams crude material is obtained.

A sample of the crude material is trapped out using GLC trapping (conditions: se 30 stainless steel 10′×⅛″ column programmed at 65°–210° C. at 6° C. per minute).

GLC profile is set forth in FIG. 1.

In order to remove the "lights" the material is microdistilled under 0.5 mm Hg pressure. The distillation is continued and the temperature in the distillation flask reaches 120° C. The residue in the distillation flask is removed and subjected to column chromatography on a 5% $H_2O$ deactivated $SiO_2$ column (850 grams). Thus, 35 grams of crude material from the distillation flask is placed on the column using the following solvents:

a. 4 liters isopentane
b. 4 liters 0.5% diethyl ether in isopentane
c. 8 liters 1% diethyl ether in isopentane The fractions are monitored using thin layer chromatography and gas chromatography. The combined fractions indicate 90% purity on GLC. The combined fractions weights about 10 grams.

The resulting combined material is again subjected to a second column chromatographic separation using undeactivated $SiO_2$, 200 grams. 9 grams of the first combined column chromatography-separated material is subjected to the column and the solvents used are as follows:

a. 1 liter isopentane
b. 0.6 liters 0.5% diethyl ether in isopentane
c. 1.5 liters 1% diethyl ether in isopentane
d. 1.5 liters 2% diethyl ether in isopentane The fractions are combined and indicate 92% purity. The weight of the resulting material is 8.5 grams.

Figure 2:
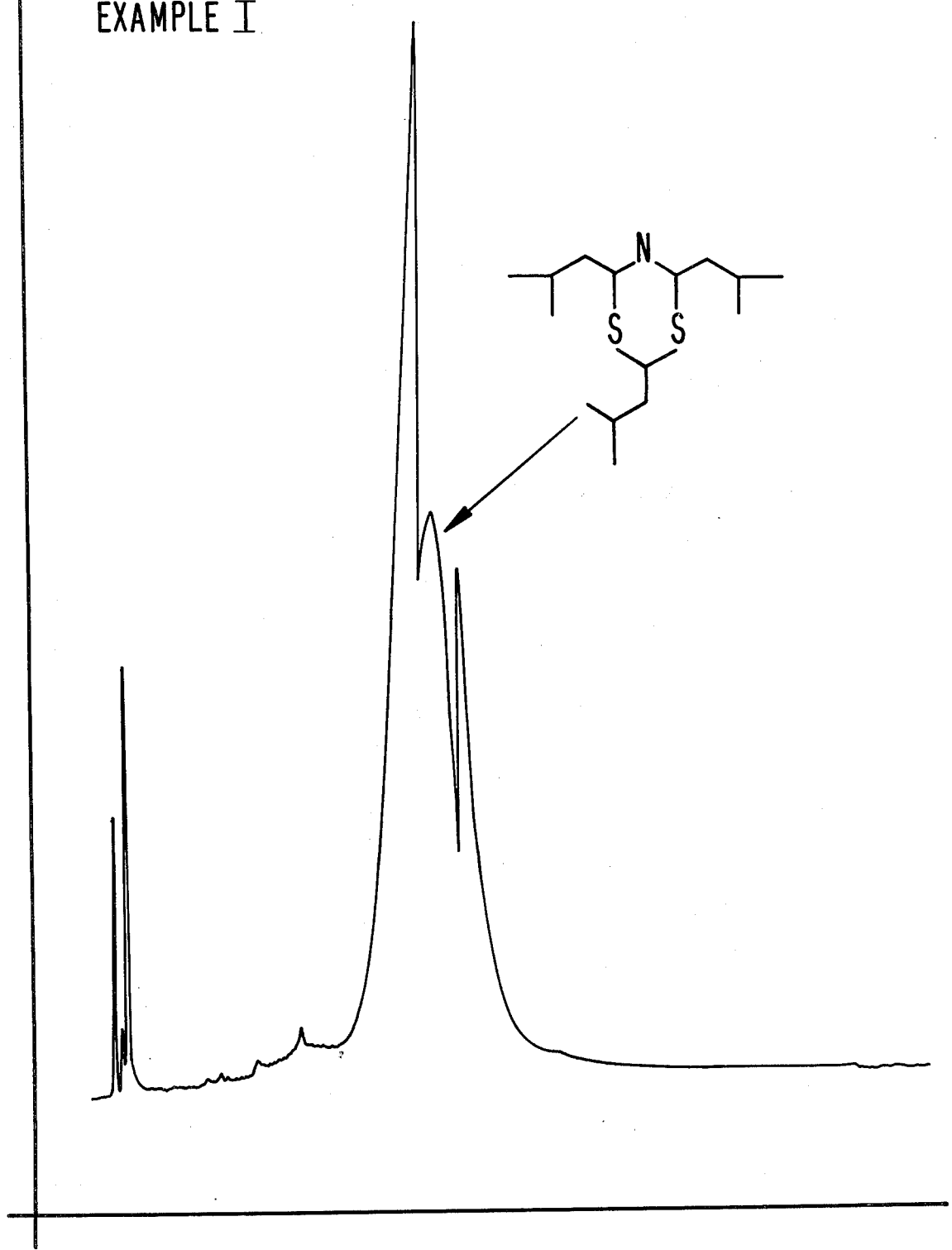
FIG. 2 is the GLC profile of the reaction produced produced according to Example I, purified by high pressure liquid chromatography (GLC conditions: Carbowax 20 m column; stainless steel 10'×⅛" programmed at 65°–210° C. at 15° C. per minute.

About 4 grams of this material obtained from the second column chromatographic separation is injected on a "Ater's" preparatory "500" high pressure liquid chromatography column. The fractions collected are monitored by thin layer chromatography. The "best" fractions observed on thin layer chromatography indicate 98% purity on GC. The high pressure liquid chromatography GC profile is set forth in FIG. 2.

The high pressure liquid chromatography conditions are:

350 ml/minute: one $SiO_2$ column chart speed 0.5 inches per minute.

The material obtained from high pressure liquid chromatography is about 2.3 grams. Fractions 17 and 18 are combined. The fractions 17 and 18 are 100% 2,4,6-tri-isobutyl-1,3,5-dithiazine having the structure:

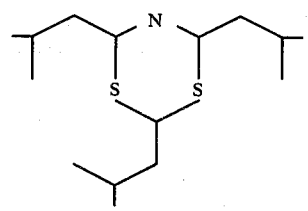

The NMR spectrum for fractions 17 and 18 of the high pressure liquid chromatography separation is set forth in FIG. 3. The IR analysis for fractions 17 and 18 resulting from the high pressure liquid chromatography separation is set forth in FIG. 4.

The GC conditions for the GC profile of the high pressure liquid chromatography separation product are:

Carbowax 20 m column: stainless steel 10′×⅛″ programmed at 65°–210° C. at 15° C. per minute.

The Mass Spectral analysis for the 2,4,6-tri-isobutyl-1,3,5-dithiazine, crystallized and purified of fractions 17 and 18 is as follows:

| M/E | Relative Intensity |
| --- | --- |
| 39 | 29 |
| 41 | 79[2] |
| 43 | 100[1] |
| 45 | 37[6] |
| 58 | 36 |
| 60 | 40[5] |
| 69 | 50[4] |
| 87 | 35 |
| 96 | 30 |
| 102 | 54[3] |
| M289 | 5 |

EXAMPLE II

The following ingredients are homogeneously admixed at 25° C.:

| INGREDIENTS | PARTS |
| --- | --- |
| Vegetable shortening | 622.7 |
| Salt | 321.7 |
| Glutamic Acid | 5.1 |
| L-Cysteine hydrochloride | 10.3 |
| Glycine | 5.1 |
| β-Alanine | 1.3 |
| Taurine | 20.0 |
| Mixture of di-sodium inosinate and | |

| INGREDIENTS | PARTS |
| --- | --- |
| di-sodium guranylate | 3.3 |

The mixture is heated to 300° F. for 30 seconds. After cooling to 100° F., 0.05 parts of 2,4,6-tri-isobutyl-1,3,5-dithiazine, crystallized and purified or substantially purified produced according to Example I are added.

The resulting mixture has an excellent bacon aroma and taste.

EXAMPLE III

Cysteine hydrochloride in the amount of 8.8 g is refluxed at 215° F. under atmospheric pressure for four hours with a mixture of 309 g of hydrolyzed vegetable protein and 674 g of water. Subsequent to the reflux, the mixture is cooled and 0.05 g of 2,4,6-tri-isobutyl-1,3,5-dithiazine, crystallized and purified or substantially purified produced according to Example I is added and intimately admixed with the composition. The mixture has an excellent fried bacon flavor of high intensity.

EXAMPLE IV

The composition prepared in Example II is dissolved in propylene glycol to provide a 0.1% solution. This solution in the amount of 0.966 g is added to 7.3 g of a soup base consisting of:

| INGREDIENTS | PARTS |
| --- | --- |
| Fine ground sodium chloride | 35.62 |
| Hydrolyzed vegetable protein | 27.40 |
| Monosodium glutamate | 17.81 |
| Sucrose | 10.96 |
| Beef fat | 5.48 |
| Sethness caramel color (powder B&C) | 2.73 |

The resulting mixture is added to 12 ounces of boiling water to obtain a soup having an excellent bacon flavor.

EXAMPLE V

The composition prepared in Exxample III is dissolved in propylene glycol to provide a 0.1% solution. This solution in the amount of 0.966 g is added to 7.3 g of a soup base consisting of:

| INGREDIENTS | PARTS |
| --- | --- |
| Fine ground sodium chloride | 35.62 |
| Hydrolyzed vegetable protein (Maggi 4BE) | 27.40 |
| Monosodium glutamate | 17.81 |
| Sucrose | 10.96 |
| Beef fat | 5.48 |
| Caramel color, bakers and confectioner's powder grade | 2.73 |

The resulting mixture is added to 12 ounces of boiling water to obtain a soup having an excellent bacon flavor.

EXAMPLE VI

One-half gram of the soup base mixture of Example IV is emulsified in a solution containing 100 g gum arabic and 300 g water. The emulsion is spray-dried with a Bowen Lab Model Drier utilizing 250 cfm of air with an inlet temperature of 500° F., an outlet temperature of 200° F., and a wheel speed of 50,000 rpm.

Twelve grams of the spray-dired material is mixed with 29.2 g of the soup base set forth in Example IV. The resulting mixture is then added to 12 ounces of boiling water and an excellent bacon flavored soup is obtained.

What is claimed is:

1. A process for producing pure crystalline or substantially pure 2,4,6-tri-isobutyl-1,3,5-dithiazine having the structure:

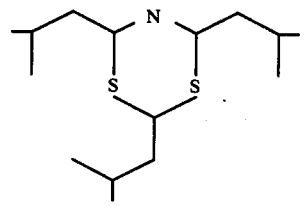

comprising, in sequential order, the steps of:
 (i) reacting ammonia with isovaleraldehyde in order to form a Shiff Base at a temperature of between −15° C. and 0° C., the mole ratio of ammonia:isovaleraldehyde being between 2:1 and 1:0.5;
 (ii) reacting said Shiff Base with hydrogen sulfide at room temperature and at atmospheric pressure over a period of time of between 1 and 5 hours thereby forming a reaction mixture;
 (iii) extracting the reaction mixture with an inert organic solvent, drying the extract-solvent mixture and evaporating the solvent therefrom;
 (iv) distilling the resulting crude material in order to remove low boiling fractions at under 0.5 mm Hg pressure and continuing distillation until the temperature of the residue reaches 120° C.;
 (v) subjecting the extracted material to column chromatography whereby selected column chromatography fractions are formed, using isopentane and diethyl ether solvents whereby selected column chromatography fractions are formed;
 (vi) subjecting said selected column chromatography fractions to high pressure liquid chromatography at 350 ml per minute in a high pressure liquid chromatography column using diethyl ether and isopentane solvents; and
 (vii) obtaining selected high pressure liquid chromatography fractions and selecting those fractions which contain substantially pure or 100% pure crystalline 2,4,6-tri-isobutyl-1,3,5-dithiazine having the structure:

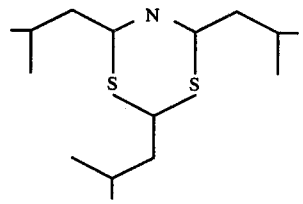

2. The process of claim 1 wherein the mole ratio of ammonia:isovaleraldehyde is 1:1.5 and the time of reaction of the Shiff Base with hydrogen sulfide is between 2 and 3 hours.

* * * * *